United States Patent [19]

Bast et al.

[11] 4,061,408
[45] Dec. 6, 1977

[54] CONNECTOR FOR A PLATE ELECTRODE

[75] Inventors: Kenneth D. Bast, St. Paul; Jerauld M. Kennelly, Mahtomedi, both of Minn.

[73] Assignee: Minnesota Mining and Manufacturing Company, St. Paul, Minn.

[21] Appl. No.: 720,743

[22] Filed: Sept. 7, 1976

[51] Int. Cl.² .......................................... H01R 13/62
[52] U.S. Cl. .......................... 339/75 R; 128/DIG. 4; 128/416
[58] Field of Search .................. 339/75 R, 17, 266 R, 339/266 G, 274, 17 F; 128/DIG. 4, 416

[56] References Cited

U.S. PATENT DOCUMENTS 3,671,924 6/1972 Nagano ............................. 339/274 X
3,824,529 7/1974 Dorrell ............................. 339/274 X Primary Examiner—Roy Lake
Assistant Examiner—E. F. Desmond
Attorney, Agent, or Firm—Cruzan Alexander; Donald M. Sell; Gary L. Griswold

[57] ABSTRACT

A lever actuated connector for a plate electrode useful in electrosurgery.

10 Claims, 11 Drawing Figures

CONNECTOR FOR A PLATE ELECTRODE

This invention relates to connectors for plate electrodes, specifically electrosurigal grounding plate electrodes. Particularly, this invention relates to a small, lightweight electrical connector which is capable of connecting to and firmly holding electrosurgical grounding plate electrodes which are flat at their connecting point without the necessity of perforations through or flanges on the plate electrode.

The use of electrosurgical grounding plate electrodes in electrosurgery is necessary in order to provide a means by which the current from the electrosurgical unit flowing to and through the cauterizing or cutting tip held by the surgeon can pass through the patient and return to the electrosurgical unit without producing a burn on the patient. If the grounding plate electrode is not present, the current can pass to the nearest ground and burn the patient at that point. Various electrosurgical grounding plates are utilized in electrosurgery including, for example, cardboard plates with aluminum skins, stainless steel plates, and foam-backed, film/metal foil laminates. U.S. Pat. No. 3,543,760 describes the first type of electrode.

Various clamps or connectors for use in connecting the grounding plate electrodes to the connector cable attached to the electrosurgical unit have been utilized. For example, U.S. Pat. No. 3,624,590 describes a large clamp containing biased jaws for attaching to the electrode plates of the type containing a flange or containing a hole for receiving a projection from the clamp. The same clamping means are also described in U.S. Pat. No. 3,642,008 which also describes a test circuit for use in an electrosurgical unit. U.S. Pat. Nos. 3,699,968 and 3,817,253 are additional examples of the projection type of clamp. A clamp of a different design which utilizes a lever or toggle-lever arm approach is U.S. Pat. No. 3,842,394. This patent describes a large clamp whereby the jaws of the clamp are moved by means of the toggle or lever arm. The lever arm combines with an adjustable spring or screw means to allow for varying thicknesses of grounding plate electrodes.

Applicants have discovered a small, lightweight connector useful in electrosurgery as a means of attaching the electrosurgical grounding plate electrode to a cable attached to the electrosurgical unit. Applicants' connector provides a simple lever means for opening and closing the connector and will firmly attach to and conduct electricity from varying types and thicknesses of electrosurgical grounding plate electrodes without the necessity of a perforation through or a flange on said electrodes.

Applicants' connector comprises a connector for a plate electrode comprising in combination a resilient body comprising an upper member and a lower member spaced from each other at one end thereof and rigidly attached to each other at the opposite end thereof; flexible, resilient first electrically conductive means adjacent said upper member; means holding said first electrically conductive means between said upper and lower members and adjacent said upper member, at least a portion of the surface of said first electrically conductive means nonadjacent to said upper member containing means for resisting movement of said plate electrode from between said first electrically conductive means and said lower member, a pivoting lever means attached to said upper member and having one end thereof adjacent said first electrically conductive means, said lever means adapted to move from a first open position whereby said first electrically conductive means is adjacent said upper member to a second closed position where said first electrically conductive means is adjacent said lower member with said plate electrode held between said first electrically conductive means and said lower member, and second electrically conductive means attached to said first electrically conductive means for electrically connecting said first electrically conductive means to an electrical power source.

Applicants invention will be more fully described with reference to the following drawings in which FIG. 1 is a shortened perspective view of the one embodiment of the connector of the present invention in use;

Figure 1:
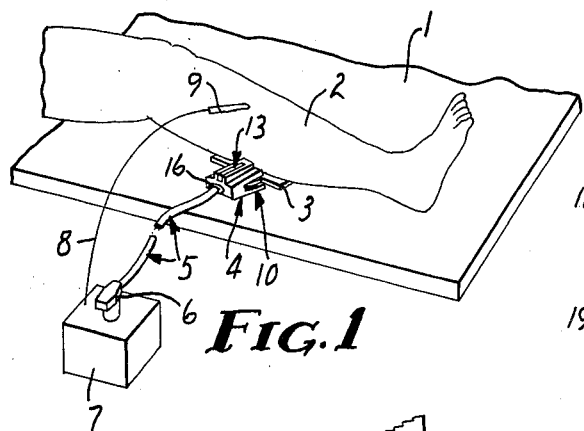

Referring to the figures in more detail, FIG. 1 depicts a surgical table 1 with the patient's leg 2 adjacent thereto. Underneath and extending from the edge of the leg 2 is a grounding plate electrode 3 which is attached to the connector 4 which is in turn connected to cable 5. Cable 5 is attached by means of plug 6 to an electrosurgical unit depicted by box 7. Extending from the electrosurgical unit is cable 8 which leads to the cauterizing or cutting tip 9 adjacent to leg 2. In use the surgeon holds tip 9 and performs the surgical technique required. The current flows from electrosurgical unit 7 through cable 8 through tip 9 into and through leg 2 and passes from the patient through grounding plate electrode 3. The current then passes from grounding plate electrode 3 through clamp 4 and cable 5 and plug 6 back to the electrosurgical unit.

Figure 2:
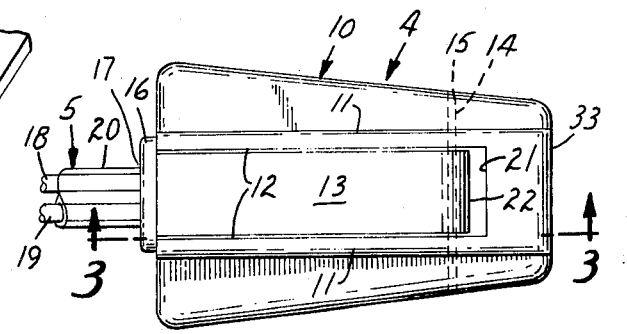
FIG. 2 depicts the top view of one embodiment of the connector of the present invention.

The connector 4 is shown by means of a top view in FIG. 2. The connector 4 comprises body 10 having a trapezoidal shape and containing raised portions 11 which form a recess 12 into which L-shaped lever arm 13 extends in the closed position of the connector. The lever arm 13 pivots on rod 14 in hole 15 in the body 10. Body 10 also contains a protrusion 16 which surrounds opening 17 for the cable 5. Cable 5 comprises electrical conductive wires 18 and 19 and insulation 20. Body 10 also contains perforation 21 which provides the space for the pivoting of lever arm 13. Connector 4 is shown in FIG. 2 in the closed position with lever arm 13 in recess 12.

Figure 3:
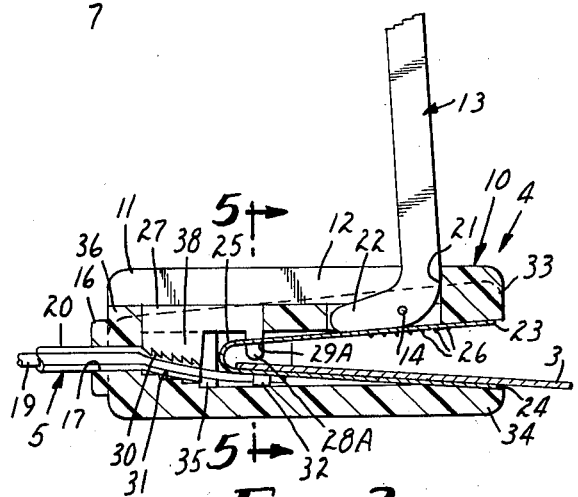
FIG. 3 depicts a sectional view of the connector shown in FIG. 2 taken along line 3—3 and shows the connector in the open position.

In FIG. 3, the connector 4 is shown in the open position with lever 13 in the up-raised position and extending outwardly from recess 12. The short end 22 of lever 13 has retracted into opening 21 in body 10. Adjacent to the shortened end 22 of lever 13 is a resilient, flexible electrically conductive sheet 23. This sheet is connected to and continuous with angular portion 25 and bottom sheet 24 of the same material. Sheet material 23 and 24 contain raised portions 26 which are visible only on sheet material 23. These raised portions while not perforating the grounding plate electrode, increase the coefficient of friction of the sheet material so that the sheet material resists slippage of the electrode 3 from the connector when the connector is in the closed position. The sheet material 23, 24, 25 forms an intimate electrical connection with the electrical grounding plate 3 comprising a film/metal foil laminate.

The conductive sheet material 23, 24, 25 is held in place by means of piece 27 which is force-fit into the body 10 of the connector 4. Piece 27 contains protrusions 28A, 28B (not shown) which pass through holes 29A, 29B (not shown) in the sheet material 23. Piece 27 also holds in place cable 5 by means of the serrated edge 30 which works with the serrated edge 31 of body 10 to hold the cable in place. Wire 19 as well as wire 18 (not visible) combine and are soldered to loop 32 on sheet material 24 to form an electrical connection between the sheet material 23, 24, 25 and cable 5.

FIG. 3 also shows the placement of the electrode 3 in the opening of the conductive sheet material 23, 24, 25. The conductive sheet material 23, 24, 25 resides between upper member 33 and lower member 34 of the body 10. The rear portion of conductive sheet material 23, 24, 25 at the bent portion 25 resides at the forward portion 35 of the back wall 36 of the body. The body 10 of the connector 4 as well as lever arm 13, and piece 27, are normally made of resilient moldable plastic material such as glass-filled polypropylene or polycarbonate. Other filled polymeric materials which are strong and impact resistant but yet have structural as well as resilient characteristics to allow the body 10, particularly upper member 33 and lower member 34, to flex to accommodate varying sizes of electrode plates 3 are useful.

Figure 4:
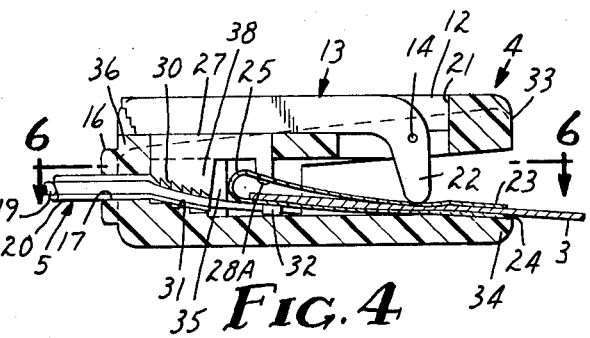
FIG. 4 is a sectional view of the connector shown in FIG. 2 taken along line 3—3 and shows the connector in the closed position.

FIG. 4 depicts connector 4 in the closed position. In this case, the L-shaped lever 13 has been rotated so that the long portion of the lever is in recess 12 in body 10. The short portion 22 of L-shaped lever 13 has been rotated so the short portion 22 has moved conductive sheet material 23 down against electrode 3. The electrode 3 is firmly affixed between conductive sheet material 23 and conductive sheet material 24 and by means of the raised portions (not shown in FIG. 4) on conductive sheet material 23 and 24 the electrode is prevented from being removed from the connector 4. The lever 13 is pivoted on rod 14 just past center so that it is difficult to easily move the lever 13 from the closed position shown in FIG. 4 to the open position shown in FIG. 3. The connector 4 can be attached to varying thicknesses of grounding plate electrodes. Increased thicknesses in the plate electrode are absorbed by the flexible, resilient upper member 33 and lower member 34 of the body 10. The film/metal foil-foam backed electrode 3 is normally 0.5 millimeter thick at the connecting point. Stainless steel electrodes are approximately of the same thickness while foil covered cardboard electrodes tend to be somewhat thicker. The raised portions on sheet material 23 and 24 preferably do not penetrate through the electrode, but merely roughen the surface of the electrode or raise the coefficient of friction between the electrode 3 and the conductive sheet material 23 and 24 so as to prevent easy removal of the electrode 3 from the connector 4. By roughening the surface of the electrode, the raised portions of sheet material 23, 24 also enhance the electrical connection between the electrode 3 and sheet material 23, 24. Normally the raised portions are 0.25 millimeter in height.

In use the clamp would be in the open position shown in FIG. 3 and the electrode 3 would be placed between conductive sheet materials 23, 24. The pivoting L-shaped lever 13 is pushed down in the closed position shown in FIG. 4 to lock the electrode in place in the connector 4. It should be noted that the force applied to sheet material 23 by short portion 22 of lever 13 is downward even though short portion 22 moves longitudinally along sheet material 23. Therefore, the longitudinal movement of portion 22 is converted to a downward force and does not act to expel electrode 3 from the connector 4.

Figure 5:
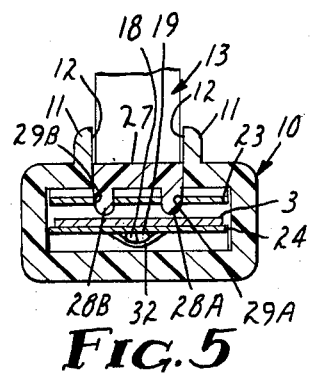
FIG. 5 is a sectional view of the connector shown in FIG. 3 taken along line 5—5.

FIG. 5 depicts a sectional view of connector 4 taken along line 5—5 in FIG. 3. In this view the connecting loop 32 for the wires 18, 19 is more clearly shown. Also, the recess 12 in body 10 is more readily apparent. Two protrusions 28A, 28B pass through holes 29A, 29B in the conductive sheet material 23. The width of conductive sheet material 23 and 24 a well as the width of the connecting portion of the electrode 3 can also be seen in this view. The cross-section of body 10 is basically rectangular.

Figure 6:
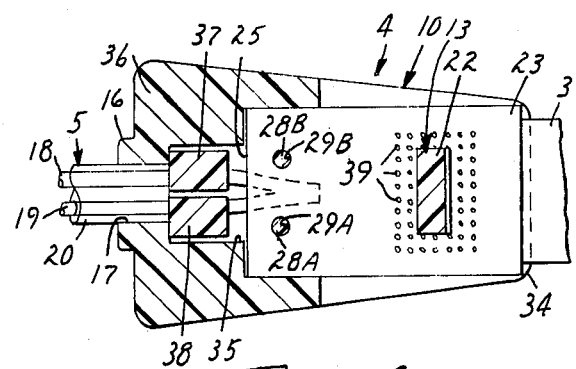
FIG. 6 is a sectional view of the connector shown in FIG. 4 taken along line 6—6.

FIG. 6 is a sectional view taken along line 6—6 of FIG. 4 and shows that the plug 27 has two portions 37, 38. Plug 27 is split in this fashion so that the plug is more easily press-fit into body 10. The location of protrusions 28A, 28B in respect to sheet material 23 as well as the location of wires 18 and 19 is more readily apparent in this view. The pattern of the raised portion 26 (not shown) of conductive sheet material 23 is evidenced by the backside thereof 39. The location and configuration of the short portion 22 of the L-shaped lever 13 is also shown in this view.

FIGS. 7 through 11 depict another embodiment of the connector of the present invention. The connector in FIGS. 7 through 11 is the type that would be used with a testing circuit as described in U.S. Pat. No. 3,642,008. In order to allow for such use, the clamp must be capable of having two separate conductive circuits pass through it. The testing circuit allows one to determine whether or not the connector is in fact attached to the electrode. If not, normally an alarm or light is activated to tell the user that the electrode is not so connected.

In the connector depicted in FIGS. 7-11, the body 40 of the connector 41 is of the same general shape as that previously described. The body 40 contains recess 42 for L-shaped lever 43. L-shaped lever 43 pivots on rod 44 in hole 45 in body 40. Recess 42 is formed in raised portions 46 in body 40. In this case the raised portions extend over a greater portion of the connector 41 than in the embodiment described above. Body 40 also contains protrusion 47, containing hole 47A through which cable 48 passes. Cable 48 comprises wires 49, 50 and insulation 51.

Figure 7:
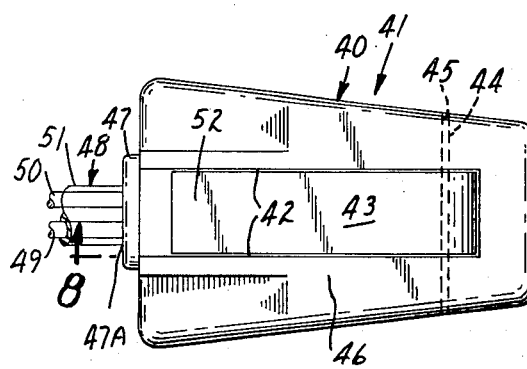
FIG. 7 is a top view of another embodiment of the connector of the present invention.
Figure 8:
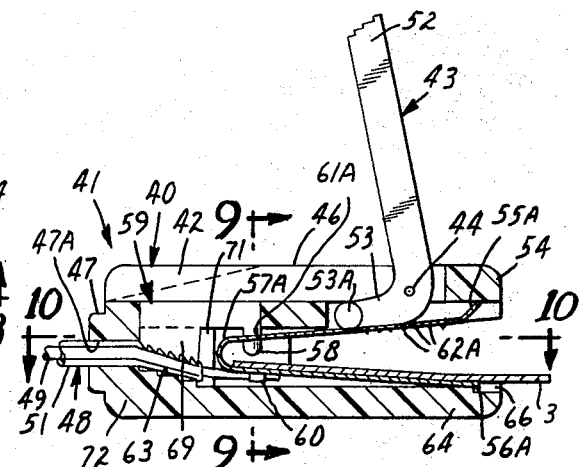
FIG. 8 is a sectional view taken along line 8—8 of the connector of FIG. 7.

FIG. 8 is a sectional view taken along line 8—8 of FIG. 7 showing the connector of FIG. 7 in the open position. As shown in FIG. 8, the connector 41 comprises body 40, L-shaped lever 43 in the open position with the long portion 52 out of recess 42 in body 40. The short portion 53 of lever 43 is adjacent the upper member 54 of body 40. The conductive sheet material in connector 41 comprises conductive sheet material 55A which has behind it conductive sheet material 55B (not shown). Conductive sheet material 55A and 55B are connected to conductive sheet material 56A and 56B (not shown), respectively by means of angular portions 57A and 57B (not shown), respectively. Between conductive sheet material 55A and 56A is electrode 3. The conductive sheet material 55A, 56A and 57A is held in place by means of protrusion 58 from plug 59 which is force-fit into body 40. Protrusion 58 passes through conductive sheet material 55A by means of hole 61A. Plug 59 also holds in place cable 48 containing insulation 51 and wire 49, 50 (not shown). Body 40 contains serrated edge 63 which assists in preventing the cable 48 from being pulled from body 40. Wire 49 is attached to conductive sheet material 56A by means of loop 60 and solder (not shown). Conductive sheet material 55A contains a raised surface 62A which is similar to that of the embodiment of the connector of the present invention described in reference to FIGS. 1–6. Sheet material 56A has a similar raised surface but this is not shown. Conductive sheet material 56A is adjacent lower member 64 of body 40.

Figure 9:
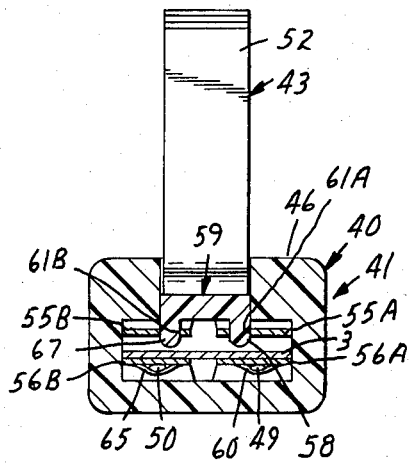
FIG. 9 is a sectional view taken along line 9—9 of the connector shown in FIG. 8.

FIG. 9 is a sectional view taken along line 9—9 of FIG. 8 and shows the rectangular configuration of body 40 of connector 41. Also shown are both conductive sheet materials 55A and 55B as well as conductive sheet materials 56A and 56B. Loop 60 for wire 49 is also shown as well as loop 65 which holds wire 50. Both wires are held in place by means of soldering. The attachment of conductive sheet material 55A by means of protrusion 58 and 55B by means of protrusion 67 is more clearly shown in this view. The grounding plate electrode 3 is also shown in this view.

Figure 10:
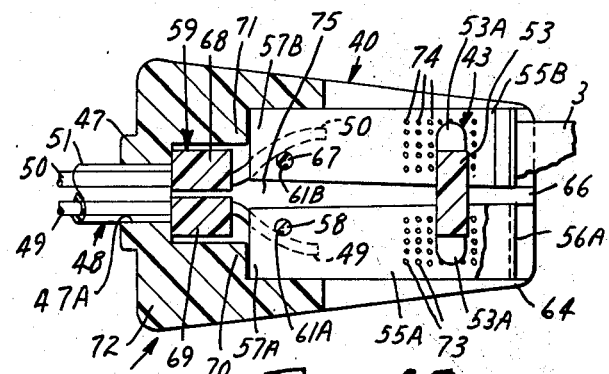
FIG. 10 is a sectional view of the connector shown in FIG. 8, in the closed position, taken along line 10—10 of FIG. 8.

FIG. 10, while being a section taken along line 10—10 of FIG. 8, is a section of the connector in the closed position. With reference to FIG. 8, the L-shaped lever arm 43 is moved down so that the long end 52 is within recess 42. Short end 53 of lever 43 (not shown) contains knobs 53A which with short end 53 press conductive sheet material 55A and 55B against electrode 3. This embodiment of the connector also is capable of accommodating varying sizes of electrode thicknesses and absorbs the thickness by flexure of the flexible, resilient body 40, particularly upper member 54 (not shown) and lower member 64.

FIG. 10 more clearly shows the configuration of plug 59 containing two halves, 68 and 69, which allow the plug 59 to be more readily press-fit into body 40. The location of protrusions 58 and 67 holding conductive sheet material 55A and 55B in place is more observable in this view as is the placement of wires 49, 50. The location of angular portion 57A and 57B of conductive sheet material against the forward portions 70 and 71 of the back 72 of body 40 is shown in this view. The configuration of the raised portion on the conductive sheet material 55A and 55B is seen in this view by the backside thereof which is numbered 73 and 74, respectively.

Figure 11:
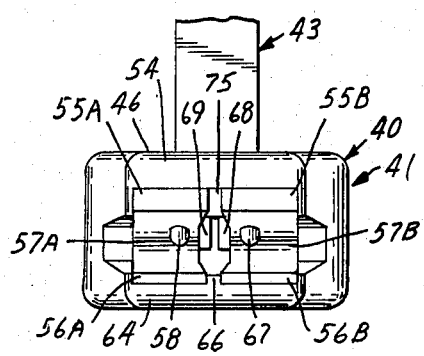
FIG. 11 is an end view of the connector of FIGS. 7–10.

An end view of the connector shown in FIGS. 7–10 is depicted in FIG. 11. Connector 41 containing L-shaped lever arm 43 is shown. All that can be seen in this view is body 40, protrusions 58 and 67 holding conductive sheet material 55A and 55B respectively in place, which in turn are connected to angular portion of the sheet material 57A and 57B and sheet material 56A and 56B, respectively. The conductive sheet material 55A, 56A and 55B, 56B contains bent ends to allow for easier submission of the electrode into the connector 41 and to assist in securing the sheet material in the body 40. Split halves 68 and 69 of plug 59 are also shown in this view. The electrode is not shown in FIG. 11. In this view the space 75 between conductive sheet material 55A and 55B and ridge 66 holding apart conductive sheet material 56A and 56B is clearly visible.

In each of the embodiments shown of the connector of the present invention, other means of attaching the conductive sheet material within the body of the connector, of course, may be utilized, such as staking or bolting.

The conductive sheet material is normally made of a metallic material which has flexibility and is resilient. Examples of materials that can be used are spring steel and beryllium-copper alloy. The material must readily conduct electricity and must, in the instance of the upper conductive sheet material which is moved by the L-shaped lever arm, be resilient and flexible.

It is preferred that the conductive sheet material in the connector be continuous from the upper portion to the lower portion and that the lower portion be present. This allows the connector to be used with electrodes which have only one conductive face yet does not require that the connector be attached in any particularly up/down relationship to the electrode. However, such continuity is not required and the lower portion of the conductive sheet material need not be present at all if the cable from the electrosurgical machine is attached to the upper portion of the sheet material and if the conductive sheet material is adjacent the conductive face of the electrode. It is however preferred that there be a raised portion on the lower member of the body of the connector to insure retention of the electrode within the connector.

A method for making the connector of the present invention is by molding the body, the L-shaped lever arm, and the plug. The L-shaped lever arm is attached to the body by means of a rod or pin. The cable is attached to the conductive sheet material by means of soldering the wires to the conductive sheet material at the loop(s) after the cable has been passed through the body. The cable and conductive sheet material is then affixed into place by force-fitting the plug into the body and through the holes in the conductive sheet material.

Various modifications of the connectors specifically described herein will become apparent to those skilled in the art. These are deemed to be within the claims which are set forth below.

What is claimed is:

1. A connector for a plate electrode comprising in combination a resilient body comprising an upper member and a lower member spaced from each other at one end thereof and rigidly attached to each other at the opposite end thereof; flexible, resilient first electrically conductive sheet means adjacent said upper member, means holding said first electrically conductive sheet means between said upper and lower members and adjacent said upper member, at least a portion of the surface of said first electrically conductive sheet means nonadjacent to said upper member containing means for resisting movement of said plate electrode from between said first electrically conductive sheet means and said lower member, a pivoting lever means attached to said upper member and having one end thereof adjacent said first electrically conductive sheet means, said lever means adapted to move from a first open position whereby said first electrically conductive sheet means is adjacent said upper member to a second closed position where said first electrically conductive sheet means is deflected to be adjacent said lower member with said plate electrode held between said first electrically conductive sheet means and said lower member and said plate electrode contacting the surface of said first electrically conductive sheet means containing means for resisting movement of said plate electrode from between said first electrically conductive sheet means and said lower member, and second electrically conductive means attached to said first electrically conductive sheet means for electrically connecting said first electrically conductive sheet means to an electrical power source.

2. The connector of claim 1 wherein said first electrically conductive sheet means comprises a multiplicity of C-shaped metallic sheets laterally separated from each other, having the upper portion of each of said sheets adjacent said upper member and the lower portion of each of said sheets adjacent said lower member; each of said metallic sheets being attached to a separate second electrically conductive means.

3. The connector of claim 2 wherein said lever means comprises an L-shaped lever.

4. The connector of claim 3 wherein said means for resisting movement comprises raised metallic portions in the facing surfaces of the upper and lower portions of said C-shaped metallic sheets.

5. A connector of claim 3 wherein said means for resisting movement comprises raised metallic portions on at least one of the facing surfaces of the upper and lower portions of said C-shaped metallic sheet.

6. The connector of claim 1 wherein said first electrically conductive sheet means comprises a C-shaped metallic sheet having its upper portion adjacent said upper member and its lower portion adjacent said lower member.

7. The connector of claim 6 wherein said lever means comprises an L-shaped lever.

8. The connector of claim 7 wherein said means for resisting movement comprises raised metallic portions on the facing surfaces of the upper and lower portions of said C-shaped metallic sheet.

9. A connector of claim 7 wherein said means for resisting movement comprises raised metallic portions on at least one of the facing surfaces of the upper and lower portions of said C-shaped metallic sheet.

10. A connector for a plate electrode comprising in combination a resilient body comprising an upper member and a lower member spaced from each other at one end thereof and rigidly attached to each other at the opposite end thereof; flexible, resilient first electrically conductive sheet means adjacent said upper member; second electrically conductive sheet means adjacent said lower member, means holding said first electrically conductive sheet means and said second electrically conductive sheet means between said upper and lower members, at least a portion of at least one facing surface of said first and second electrically conductive sheet means containing means for resisting movement of said plate electrode from between said first and second electrically conductive sheet means, a pivoting lever means attached to said upper member and having one end thereof adjacent said first electrically conductive sheet means, said lever means adapted to move from a first open position where said first electrically conductive sheet means is adjacent said upper member to a second closed position where said first electrically conductive sheet means is deflected to be adjacent said lower member with said plate electrode held between said first and second electrically conductive sheet means and said plate electrode contacting said means for resisting movement of said plate electrode from between said first and second electrically conductive sheet means, and third electrically conductive means attached to at least one of said first and second electrically conductive sheet means for electrically connecting at least one of said first and second electrically conductive sheet means to an electrical power source.

* * * * *